United States Patent
Yang (10) Patent No.: US 7,357,932 B2
(45) Date of Patent: Apr. 15, 2008

(54) **SURFACE PROTEIN OF *NEISSERIA* BACTERIA**

(75) Inventor: Chiou-Ying Yang, Taichung (TW)

(73) Assignee: Center of Disease Control Department of Health, Taipei (TW)

( * ) Notice: Subject to any disclaimer, the term of this patent is extended or adjusted under 35 U.S.C. 154(b) by 0 days.

(21) Appl. No.: 10/867,662

(22) Filed: Jun. 16, 2004

(65) Prior Publication Data

US 2005/0281835 A1 Dec. 22, 2005

(51) Int. Cl.
*A61K 39/02* (2006.01)
*A61K 38/00* (2006.01)
*A61K 39/095* (2006.01)

(52) U.S. Cl. ............... 424/190.1; 530/300; 424/234.1; 424/249.1

(58) Field of Classification Search ............... 424/190.1
See application file for complete search history.

(56) References Cited

U.S. PATENT DOCUMENTS

2005/0260581 A1* 11/2005 Fontana et al. ................ 435/6

FOREIGN PATENT DOCUMENTS

WO  WO 02/079243 A2 * 10/2002

OTHER PUBLICATIONS

Boslego, J. et al (Gonorrhea Vaccines, Chapter 17, 211-223).*
Ellis, R (New Technologies for Making Vaccines, text book, 1998, 568-575).*
Danzig, L (*Meningococcal* Vaccines, Pediatr Infect Dis J, 2004; 12 suppl: S285-92), abstract only.*
Van Der Ley, P. et al (Construction of a Multivalent *Meningococcal* Vaccine Strain Based On The Class 1 Outer Membrane Protein, Infection and Immunity, 1992; 60(8): 3156-61).*
Jones, D (*Meningococcal* Vaccines: Past, Present and Future in *Meningococcal* Disease, Cartwright, K (ED) Wiley Press, New York, USA, 1995: 147-57).*
Perkins, M. et al (Rapid Bacterial Antigen Detection Is Not Clinically Useful, Journal of Clinical Microbiology, 1995; 33(6): 1486-1491).*

* cited by examiner

*Primary Examiner*—Robert A. Zeman
*Assistant Examiner*—Lakia J Tongue
(74) *Attorney, Agent, or Firm*—Birch, Stewart, Kolasch & Birch, LLP.

(57) ABSTRACT

Present invention provides a monoclonal antibody binding to *Neisseria* bacteria and its target antigen Ag473, which include the sequences of its polynucleotide and its amino acid, wherein the *Neisseria* bacteria can be *Neisseria meningitidis* or *Neisseria gonorrhoeae*; and wherein Ag473 can be made into a vaccine or a diagnostic or therapeutic reagent.

1 Claim, 8 Drawing Sheets

```
Query:     5     ttggcggcatctttcattttgtctgccgcttcctgagccgcgtcggcggctttgttcaaa   64
                 ||||||||  |||||||||||||||||||||||||||||||||||||| |||||||||||
Sbjct: 1003584   ttggcggcgtctttcattttgtctgccgcttcctgagccgcgtcggcagctttgttcaaa   1003643

Query:    65     gtgtctttagccgcttcgcttaccgcttctttggtttcggctgccgcgtctttggcttca   124
                 ||||||||||||||||||||||||||||||||||||||||||||||||||||||||||||
Sbjct: 1003644   gtgtctttagccgcttcgcttaccgcttctttggtttcggctgccgcgtctttggcttca   1003703

Query:   125     gttacagcttcctcggcacttgcctttgcatcagccgcagcatctttgacttggcctttc   184
                 ||||||||||||||||||||||||||||||||||||||||||||||||||||||||||||
Sbjct: 1003704   gttacagcttcctcggcacttgcctttgcatcagccgcagcatctttgacttggcctttc   1003763

Query:   185     gcttcttcgacggcagaagcggcagactcggcggcagaagccgcagtgtctttaacatcg   244
                 ||||||||||||||||||||||||||||||||||||||||||||||||||||||||||||
Sbjct: 1003764   gcttcttcgacggcagaagcggcagactcggcggcagaagccgcagtgtctttaacatcg   1003823

Query:   245     gactcaacggcttgggccgcttctttaacctcctgtttggcttcttgcgaacaagctgcc   304
                 ||||||||||||||||||||||||||||||||||||||||||||||||||||||||||||
Sbjct: 1003824   gactcaacggcttgggccgcttctttaacctcctgtttggcttcttgcgaacaagctgcc   1003883

Query:   305     aaggcagccgccatcattgcggcaatcaataattttttcatg   346
                 ||||||||||||||||||||||||||||||||||||||||||
Sbjct: 1003884   aaggcagccgccatcattgcggcaatcaataattttttcatg   1003925
```

FIG.6

Ag473-2:   1    atgaaaaaattattgattgccgcaatgatggcggctgccttggcagcttgttcgcaagaa  60
Ag473-Ng:  1    atgaaaaaattattgattgccgcaatgatggcggctgccttggcagcttgttcgcaagaa  60

Ag473-2:   61   gccaaacaggaggttaaggaagcggttcaagccgttgagtccgatgttaaagacactgcg  120
Ag473-Ng:  61   gccaaacaggaggttaaagaagcggcccaagccgttgagtccgatgttaaagacactgcg  120

Ag473-2:   121  gcttctgccgccgagtctgccgcttctgccgtcgaagaagcgaaagaccaagtcaaagat  180
Ag473-Ng:  121  gcttctgccgccgagtctgccgcttctgccgtcgaagaagcgaaaggccaagtcaaagat  180

Ag473-2:   181  gctgcggctgatgcaaaggcaagtgccgaggaagctgtaactgaagccaaagaagctgta  240
Ag473-Ng:  181  gctgcggctgatgcaaaggcaagtgccgaggaagctgtaactgaagccaaagacgcggca  240

Ag473-2:   241  actgaagccaaagaagctgtaactgaagcagctaaagatactttgaacaaagctgccgac  300
Ag473-Ng:  241  gccgaaaccaaagaagcggtaagcgaagcggctaaagacactttgaacaaagccgccgac  300

Ag473-2:   301  gcgactcaggaagcggcagacaaaatgaaagatgccgccaaa  342
Ag473-Ng:  301  gcggctcaggaagcggcagacaaaatgaaagatgccgccaaa  342

FIG.7

```
Ag473-1 (NMB1468)   1   MKKLLIAAMM AAALAACSQE AKQEVKEAVQ AVESDVKDTA ASAAESAASA
Ag473-2             1   MKKLLIAAMM AAALAACSQE AKQEVKEAVQ AVESDVKDTA ASAAESAASA
Ag473-3             1   MKKLLIAAMM AAALAACSQE AKQEVKEAVQ AVESDVKDTA ASAAESAASA
Ag473-4             1   MKKLLIAAMM AAALAACSQE AKQEVKEAVQ AVESDVKDTA ASAAESAASA
Ag473-Ng            1   MKKLLIAAMM AAALAACSQE AKQEVKEAAQ AVESDVKDTA ASAAESAASA

Ag473 (NMB1468)    51   VEEAKDQVKD AAADAKASAE EAVTEAKEAV T--------- ----------
Ag473-2            51   VEEAKDQVKD AAADAKASAE EAVTEAKEAV TEAKEAVT-- ----------
Ag473-3            51   VEEAKDQVKD AAADAKASAE EAVTEAKEAV TEAKEAVTEA KEAVT-----
Ag473-4            51   VEEAKDQVKD AAADAKASAE EAVTEAKEAV TEAKEAVTEA KEAVTEAKEA
Ag473-Ng           51   VEEAKGQVKD AAADAKASAE EAVTEAKDAA AETKEAVS-- ----------

Ag473-1 (NMB1468)  82   --EAAKDTLN KAADATQEAA DKMKDAAK        107
Ag473-2            89   --EAAKDTLN KAADATQEAA DKMKDAAK        114
Ag473-3            96   --EAAKDTLN KAADATQEAA DKMKDAAK        121
Ag473-4           101   VTEAAKDTLN KAADATQEAA DKMKDAAK        128
Ag473-Ng           89   --EAAKDTLN KAADAAQEAA DKMKDAAK        114
```

SURFACE PROTEIN OF *NEISSERIA* BACTERIA

FIELD OF THE INVENTION

Present invention discloses a conserved surface protein of *Neisseria* bacteria, nucleotide sequences encoding such polypeptides, and its monoclonal antibody which can be made into pharmaceutical compositions including prophylactic, diagnostic or therapeutic compositions.

BACKGROUND OF THE INVENTION

*Neisseria meningitidis* a capsulated, Gram-negative bacterium, is a cause of life-threatening invasive bacterial infection, especially in young children. The organism can be classified into at least 13 serogroups based on chemically and antigenically distinctive polysaccharide capsules. Among them, serogroups A, B, C, W-135 and Y account for virtually all pathogenic isolates. Despite several decades of research, no effective vaccine that protects against all meningococcal strains is available, and diseases caused by *N. meningitidis* meningitis and septicemia, remain a serious public health problem throughout the world ENRfu (Peltola, Drugs 55: 347-366, 1998). The failure in development of effective vaccines is possibly attributed to the high antigenic diversity of the pathogen. The currently licensed vaccine is polysaccharide-based which does not include the serogroup B capsular polysaccharide, due to the poor immunogenicity of the latter substance (Frasch, Meningococcal vaccines: past, present and future. In: Meningococcal Disease. Cartwright K. (Ed.) Wiley Press, New York, USA: 145-157, 1995.). Therefore effective vaccine against disease caused by serogroup B strains, the organisms responsible for the majority of meningococcal infections in many countries, is still not available ENRfu (Verheul et al., Microbiol Rev 57:34-49, 1993).

For development of effective vaccines against serogroup B meningococci, most research has focused on the outer membrane proteins (OMPs). Of the five major OMP classes, class I OMP (also named PorA) has attracted the most attentions. This is because that PorA is expressed by most meningococci and is highly immunogenic in humans following infection or immunization (Guttormen et al., Infect. Immun 62:1437, 1994; Clasassen et al., Vaccine 14:1001, 1996; van der Ley and Poolman, Infect Immun. 60:3156, 1992). Moreover, specific antibodies induced by PorA exhibit both bactericidal activity and opsonic function (Aase et al., Scand J Immunol 47:388-396, 1998; Lehmann et al., Infect. Immun. 67:2552, 1999). However, the high degrees of antigenic and phase variation of PorA have limited the effectiveness of PorA-based vaccines to the vaccine-type strains (Fischer et al., Vaccine 17: 2377-2383, 1999). Broadened protection may be achieved by combining different PorA subtypes. For example, a hexavalent PorA vaccine composed of the most prevalent PorA variants found in the Netherlands and Western Europe has been developed (Claassen et al., 1996, Vaccine 14:1001-1008; Peeters et al, 1996, Vaccine 14:1009-1015). Nevertheless, the observation that different PorA phenotypes can emerge rapidly after its epidemic spread (Jelfs et al., Clin. Diagn. Lab. Immunol. 7:390-395, 2000; Martin et al., Vaccine 18:2476-2481, 2000) has to be considered in the development of PorA-based vaccine.

To create vaccines with a broad spectrum of protection, it is important to identify surface proteins which are highly conserved in different strains. Several proteins meet the criteria have been reported. These include P64k (U.S. Pat. No. 5,286,484), hemoglobin receptor (U.S. Pat. No. 6,121, 037), NspA (U.S. Pat. No. 6,287,574 B1), NhhA (U.S. Pat. No. 6,607,729 B2), NMASP (U.S. Pat. No. 6,693,186 B2), NadA (Comanducci et al., J. Exp. Med. 195:1445-1454, 2002), GNA1870 (Masignani et al., J. Exp. Med. 197:789-799, 2003), GNA33GNA992GNA1162GNA1220GNA1946GNA2001 and GNA2132 in which GNA1870GNA33GNA1162GNA1946 and GNA2132 are lipoproteins identified by whole genome sequencing (Pizza et al., Science 287:1816-1820, 2000). Despite the discovery of these proteins, it is still desirable to isolate more surface proteins of *N. meningitidis* which in combination with others may enhance the vaccine efficacy.

BRIEF SUMMARY OF THE INVENTION

The present invention comprises a monoclonal antibody 4-7-3, prepared from mouse immunized with the whole cells of *N. meningitidis* and its target antigen (referred to hereafter as Ag473). The antigen, estimated 10-15 kDa, is a novel lipoprotein with unknown function ubiquitous on the surface of *Neisseria* bacteria, including among others *N. meningitidis* and *N. gonorrhoeae*.

The present invention discovers five variants of Ag473 with SEQ ID No. 1, 3, 5, 7 and 9 as the isolated polynucleotide and SEQ ID No. 2, 4, 6, 8 and 10 as the isolated polypeptide (as shown in Sequence List), wherein SEQ ID No. 1 to 8 are acquired from *N. meningitidis*. The main difference among the four variants lies in the number of a stretch of 21 bp (base pair) (gaagctgtaactgaagccaaa) (SEQ ID NO: 13) corresponding to a 7-amino acid residue (EAVTEAK) (SEQ ID NO: 14) in the polypeptide sequences. SEQ ID No. 9 and 10 are obtained from *N. gonorrhoeae*, wherein SEQ ID No. 9 is 95% identical to SEQ ID No. 1 (DNA) and SEQ ID No. 10 is 90.4% identical to SEQ ID No. 2 (protein).

The present invention discovers five variants of Ag473 with SEQ ID No. 1, 3, 5, 7 and 9 as the isolated polynucleotide and SEQ ID No. 2, 4, 6, 8 and 10 as the isolated polypeptide (as shown in Sequence List), wherein SEQ ID No. 1 to 8 are acquired from *N. meningitidis*. The main difference among the four variants lies in the number of a stretch of 21 bp (base pair) (gaagctgtaactgaagccaaa) (SEQ ID NO: 13) corresponding to a 7-amino acid residue (EAVTEAK) (SEQ ID NO: 14) in the polypeptide sequences. SEQ ID No. 9 and 10 are obtained from *N. gonorrhoeae*, wherein SEQ ID No. 9 is 95% identical to SEQ ID No. I (DNA) and SEQ ID No. 10 is 90.4% identical to SEQ ID No. 2 (protein).

The present invention further encompasses the Ag473 in recombinant form and the antiserum raised using this protein. The antiserum can bind to living *N. meningitidis* resulting in bactericidal activity, showing that Ag473 has the potential to be a vaccine component and a therapeutic target.

The present invention also examines the occurrence of Ag473 protein and the corresponding gene in a number of bacterial species, using 4-7-3 antibody and colony-PCR, respectively. Positive results are only observed in the *Neisseria* bacteria, including *N. meningitidis* and *N. gonorrhoeae*. Therefore, the present invention also provides a novel way to diagnose *Neisseria* bacteria.

BRIEF DESCRIPTION OF THE DRAWINGS

The present invention will be better understood from the following detailed description of preferred embodiments of the invention, taken in conjunction with the accompanying drawings, in which.

Sequence List shows the nucleotide and amino acid sequences of the five Ag473 variants described in the present invention.

DESCRIPTION OF THE PREFERRED EMBODIMENT

The following descriptions of the preferred embodiments are provided for the purpose to understand the features and the structures of the present invention.

Figure 1:
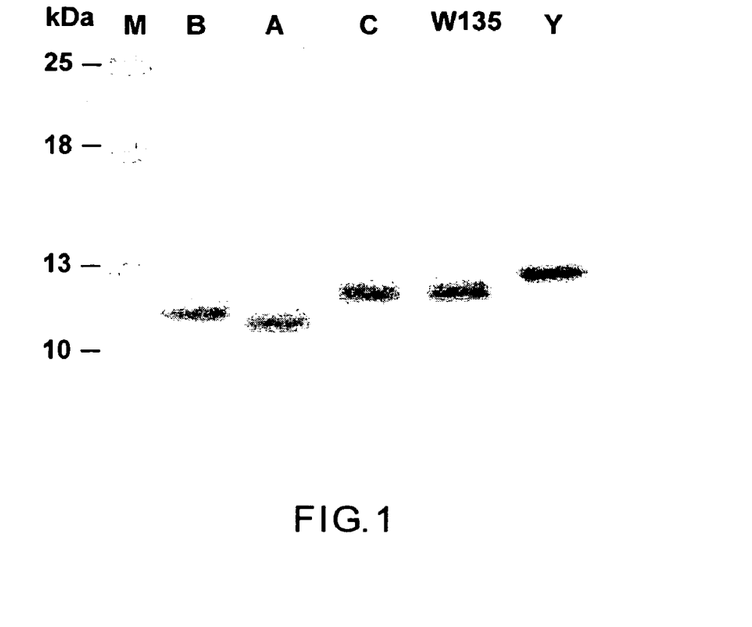
FIG. 1 shows a Western blot of the total proteins from cells of serogroups A, B, C, W-135 and Y *N. meningitidis* in which monoclonal antibody 4-7-3 was used as the primary antibody.
Figures 2A, 2B:
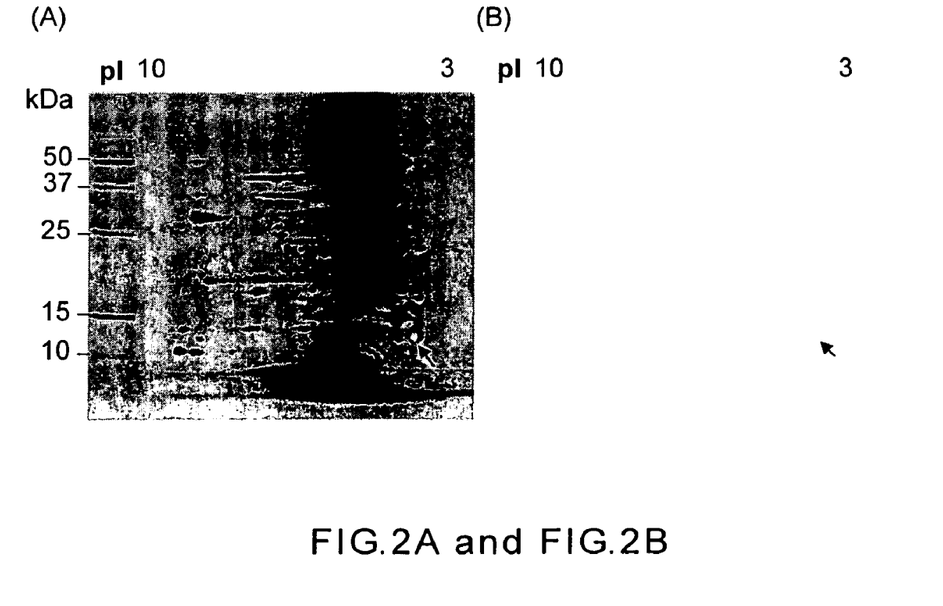
FIG. 2 shows the silver-stained 2D-gel (A) and its corresponding Western blot (B) of the total protein from *N. meningitidis* identifying the antigen for antibody 4-7-3.
Figure 3:
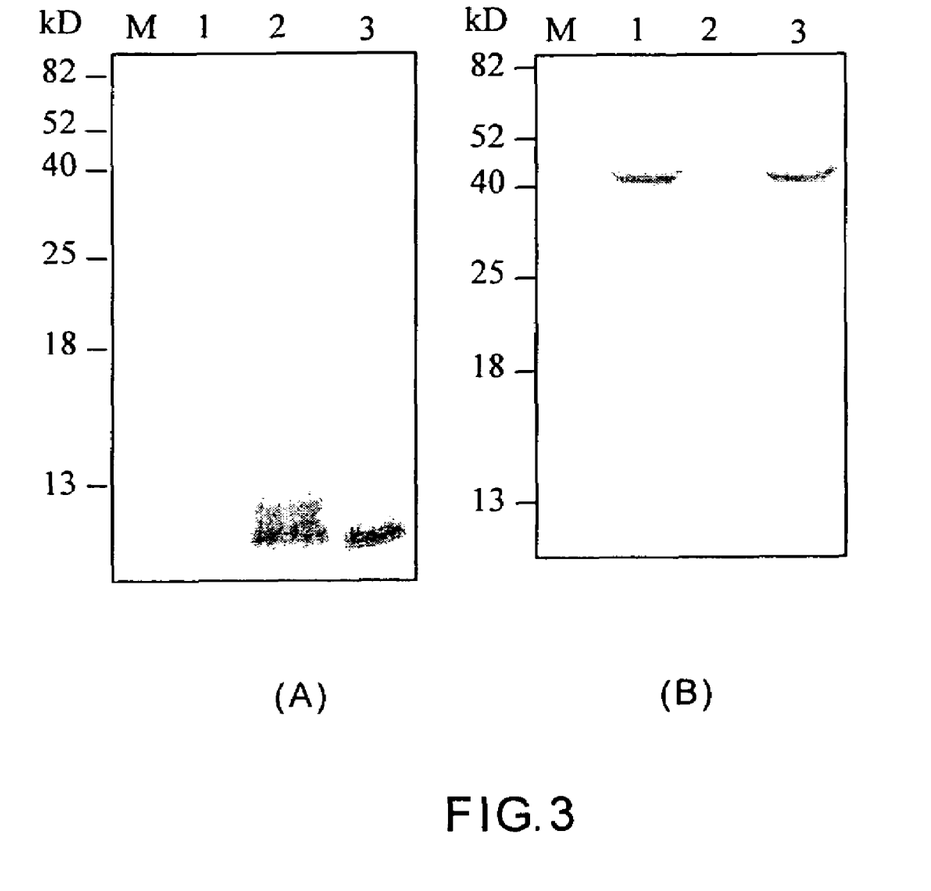
FIG. 3 shows the Western blots of the total proteins from *N. meningitidis* (lane 3), *E. coli* expressing the recombinant Ag473 (lane 2) and *N. meningitidis* in which the corresponding gene is disrupted (lane 1), wherein (A) and (B) were probed with 4-7-3 and anti-PorA, respectively.

The present invention uses the whole cells of serogroup B strain Nm22209 isolated in Taiwan as the antigen to prepare antibodies which can be used as a tool for finding surface components of *N. meningitidis* with potential to become a vaccine composition. To keep the completeness of the whole cell, bacteria were heated and injected directly for immunization.

1. Preparation and Characterization of Monoclonal Antibody (mAb) 4-7-3

(A) Mice are injected intraperitoneally with the heat-killed Nm22209 cells.

(B) Hybridomas are obtained by the fusion of spleen cells of the immunized mouse with Sp2/0-Ag14 cells.

(C) Hybridomas secreting antibodies against Nm22209 are identified by ELISA using the supernatant harvested from a culture of hybridoma cells.

(D) Supernatant harvested from hybridoma 4-7-3 shows binding activity to all *N. meningitidis* tested including 184 strains isolated in Taiwan and 3 ATCC reference strains (ATCC 13077ATCC 13090and ATCC 13102 representing serogroups A, B, and C, respectively) but not the human neuroblastoma cell line IMR-32.

(E) The bactericidal activity of purified 4-7-3 against Nm22209 is tested according to the procedures described by Martin et. al. (J. Exp. Med. 185: 1173-1183, 1997) with the following modifications. Eight μl of the bacterial suspension ($1\times10^5$ CFU/ml) is incubated with 10 μl of different concentrations of protein LA-purified 4-7-3 for 20 min at 37° C., 10 μl of human complement (40 CH50 unit/ml, Sigma Cat# S1764) is then added to the mixture. After incubation for 1 hr, 10 μl of each mixture is plated onto chocolate agar plates. The surviving colonies are counted after 18 hr of incubation of the plates in an atmosphere of 5% $CO_2$ at 37° C. It is found that approximately 6 g of 4-7-3 is required to render a 50% inhibition of bacterial growth in the experimental conditions.

(F) To reveal the entity of the antigen recognized by 4-7-3meningococci of the five different serogroups are lysed with the SDS-PAGE loading buffer (0.025 M Tris pH 8.7, 2% SDS, 10% glycerol, 0.05 mg/ml bromophenol blue), and subjected to Western blot analysis, wherein a distinct immunoreactive band located between 10-15 kDa, which may show a slight variation in size among strains, is observed from each isolate (FIG. 1).

The above results clearly demonstrate that 4-7-3 recognizes a conserved surface protein, which is able to induce a protective immune response against *N. meningitidis.*

2. Identification of the Antigen for 4-7-3 (Referred to as Ag473 Hereafter)

(A) Total proteins of the Nm22209 are separated by 2D gel electrophoresis in duplicate.

(B) One of the gels is subjected to silver staining and the other is used for blotting followed by probing with 4-7-3 to localize the Ag473 (as shown in FIG. 2).

(C) The gel containing the silver-stained spot corresponding to the immunospot in the Western blot is collected and analyzed by mass spectrometry, which shows that it can be a hypothetical protein NMB1468 composed of 107 amino acid residues in serogroup B meningococcal strain MC58. DOLOP analysis (Madan Babu and Sankaran, Bioinformatics 18:641-643, 2002) shows that this hypothetical protein can be a lipoprotein. Though the DNA sequence is also present in the genome of serogroup A meningococcal strain A Z2491 (AL162756), it is included as a part of protein annotated to encode a 979 aa.

(D) Related art shows that the promoter of NM can function in *E. coli*. (Sawaya et al., Gene 233:49-57, 1999). To clarify if NMB1468 is the homolog of Ag473PCR primers are designed according to the genome sequence of MC58. The DNA fragment encompassing the annotated open reading frame and the upstream 329 bp is amplified from Nm22209 by PCR, cloned into vector pGEM-T-Easy, and transformed into *E. coli* HB101. Total proteins from the transformed and non-transformed HB101 are subjected to Western blot analysis. In the meantime, a genetic engineered Nm22209 with a disrupted Ag473 gene is also generated. Therein, the recombinant protein expressed in transformed *E. coli* can be identified by antibody 4-7-3but no immunoreactive bands are observed in the mutated Nm22209 (as shown in FIG. 3).

The above results clearly demonstrate that Ag473 is a homolog of NMB1468 which is an expressed protein in *N. meningitids.*

3. Sequence Analysis of the Ag473 Gene

Sequence analysis of the above PCR product reveals (SEQ ID NO. 1) an additional 12-bp direct repeat in the coding region comparing to that (SEQ ID NO. 3) of NMB11468 in MC58. This repeat is not found in neither the genome sequence of MC58 nor Z2491 strains. As a result, Ag473 comprises 114 amino acid residues with a two 7-amino acid (Glu-Ala-Val-Thr-Glu-Ala-Lys) (SEQ ID NO: 14) tandem repeats (SEQ IS NO. 2; those underlined).

Western blotting shows that the immunoreactive bands detected by 4-7-3 are slightly varied in size among different meningococcal strains (as shown in FIG. 1), which implies that there might be different variants of Ag473.

To investigate the degrees of variation, the Ag473 genes of ten meningococcal strains, including the above five strains used in the Western blot analysis, are amplified by PCR, cloned into plasmid pGEM-T-Easy, and subjected to nucleotide sequencing. Four sequences (SEQ ID NO. 1, 3, 5, 7) different mainly on the numbers of the 21-bp direct repeat (those underlined) are found. The smallest gene has the same sequence (SEQ ID NO. 3) as NMB1468 with only one 21-bp repeat while the longest gene has four 21-bp repeats in tandem (SEQ ID NO. 7). As a consequence, the coding proteins contain 107, 114, 121 and 128 amino acids, respectively. (Please refer to SEQ ID NO. 2, 4, 6, 8 and FIG. 8)

Figure 4A:
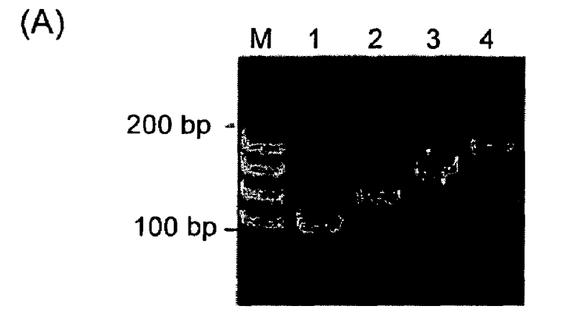
FIG. 4 shows a photograph of ethidium bromide-stained polyacrylamide gel of the PCR products (A) amplified with the primers flanking the 21-bp repeat region of the four gene variants as depicted on panel B. The regions where primers annealed with are underlined and marked with arrows in FIG. 7.
Figure 4B:
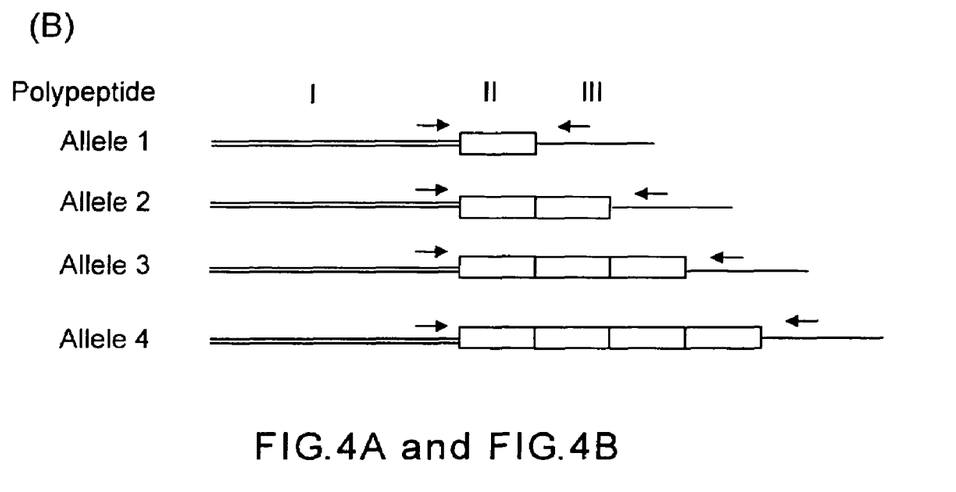

To access the numbers of Ag473 gene allele in meningococcal population, DNA fragments spanning the 21-bp repeat region are obtained from 141 strains, including the three ATCC strains mentioned above, by PCR amplification with the primers flanking the repeated region and the products are analyzed by polyacrylamide gel electrophoresis which shows that only four different sizes are present. A representative result is shown in FIG. 4A. The regions that the primers annealed to are indicated with an arrow in the Ag473-2 sequence of FIG. 7 and SEQ ID NO. 1.

Figure 5A:
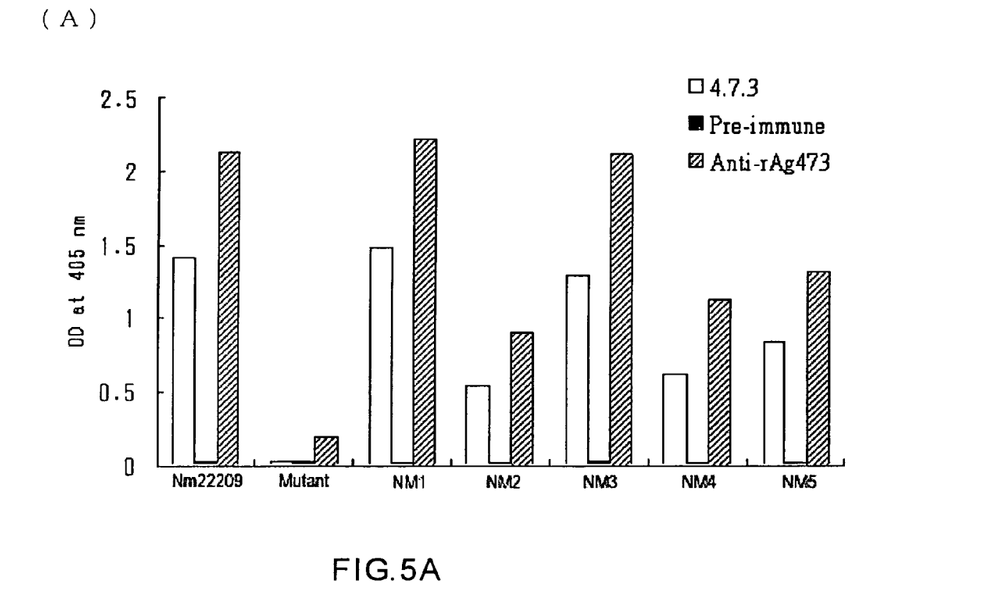
FIG. 5 shows the binding of anti-Ag473 antiserum to intact *N. meningitidis* determined by ELISA (5A) and the fluorescent activated cell scanning (FACS) analysis (5B).
Figure 5B:
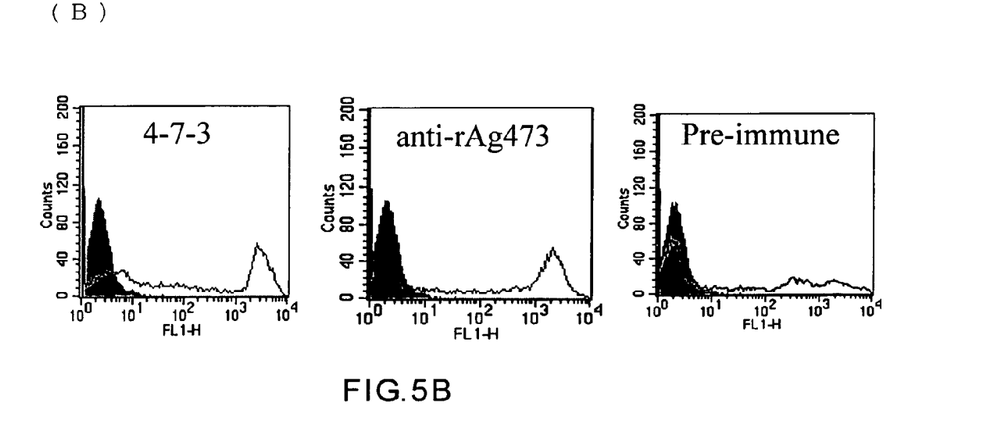

4. The Immunogenicity Test of the Recombinant Ag473 (rAg473):

To prove that Ag473 can be used as a vaccine component, recombinant Ag473 is produced in *E. coli* and used to immunize mice. The ability of the anti-rAg473 to recognize meningococci is demonstrated by whole cell-ELISA and FACS analysis (as shown in FIG. 5), wherein Nm22209 is a vaccine strain for preparing the antibody 4-7-3; Nm22209::Ag473(Gm)[Nm22209(Ag473::Gm)] is the mutant with a disrupted Ag473 gene; NM1 and NM2 are the clinical isolates; NM3NM4 and NM5 are the reference strains of serogroup A, B and C from American Type Culture Collection (ATCC), respectively.

Additionally, In vitro bactericidal activity test as described above shows that the anti-rAg473 is effective in killing NM22208. Accordingly, Ag473 is proved to be able to induce immune response against the whole cells of *N. menigitidis* and has the potential to be made into a vaccine.

5. Expression of Ag473 in *N. gonorrhoeae*

Figure 6:
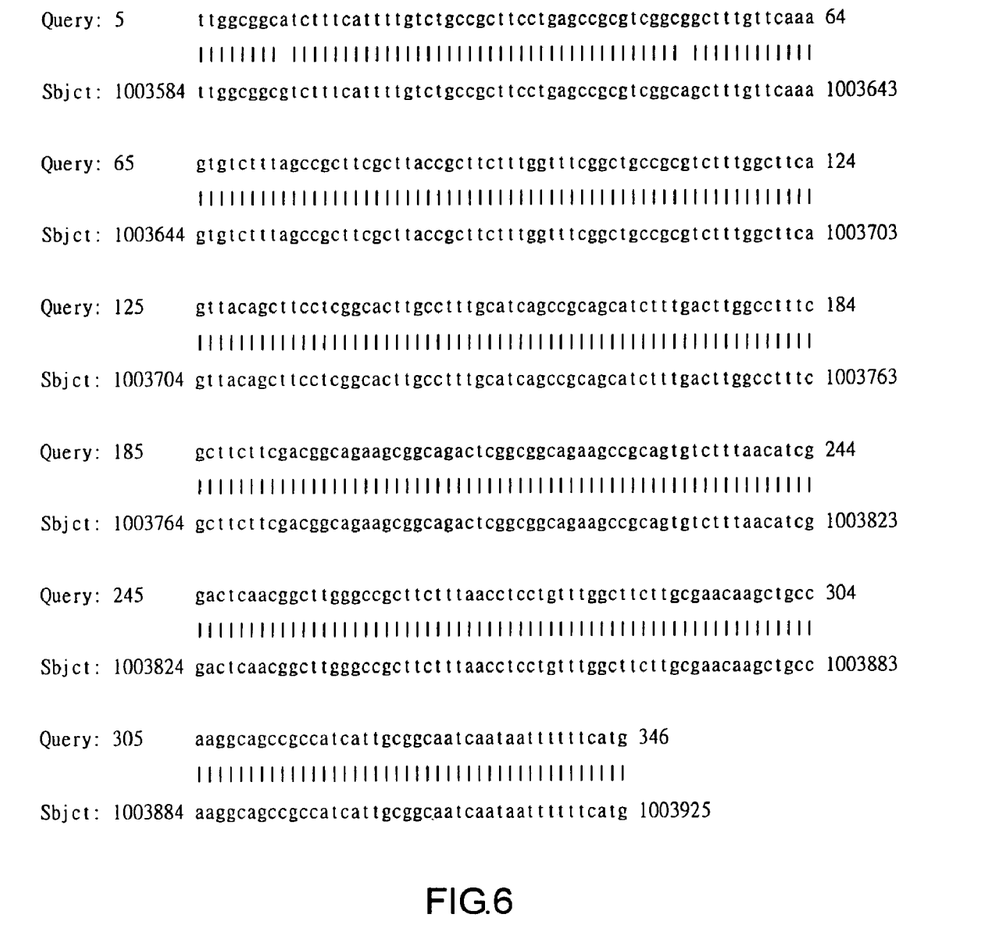
FIG. 6 aligns SEQ ID No. 11 (query) with the homologue from the genome of N. gonorrhoeae (sbjct) (SEQ ID NO: 12).
Figure 7:
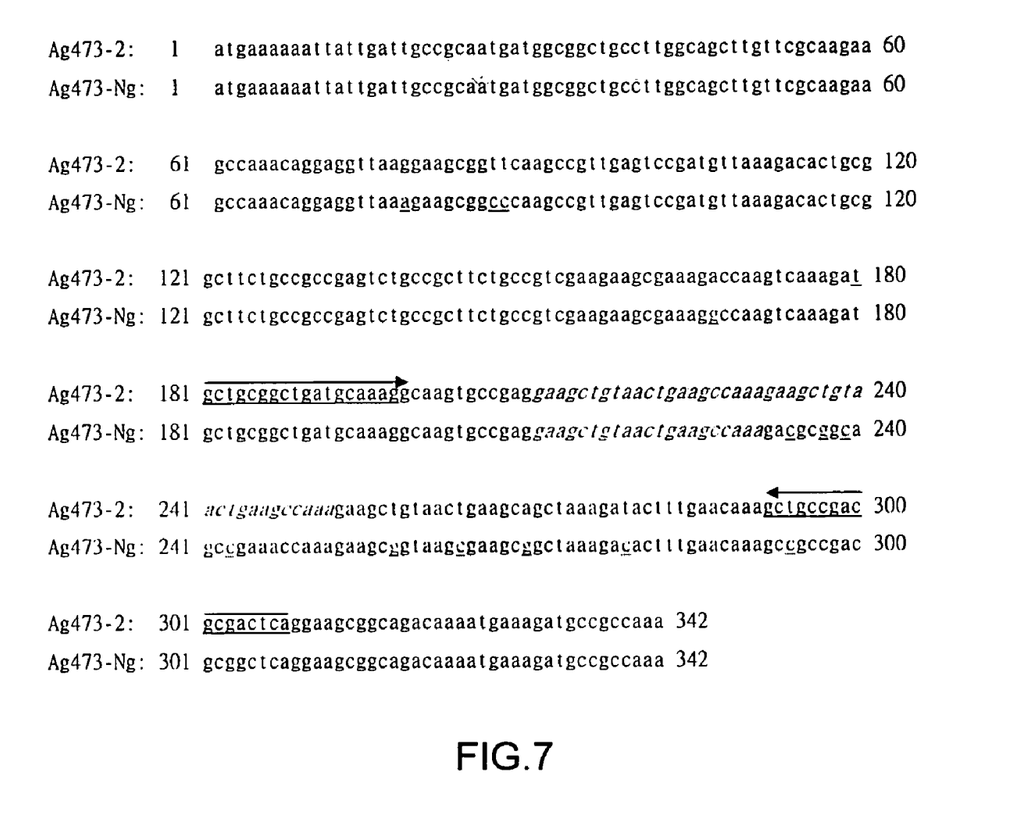
FIG. 7 aligns SEQ ID No. 1 (Ag473-2) with SEQ ID NO. 9 (Ag473-Ng), wherein the mismatched nucleotides are capitalized and the 21-bp repeat are italicized.
Figure 8:
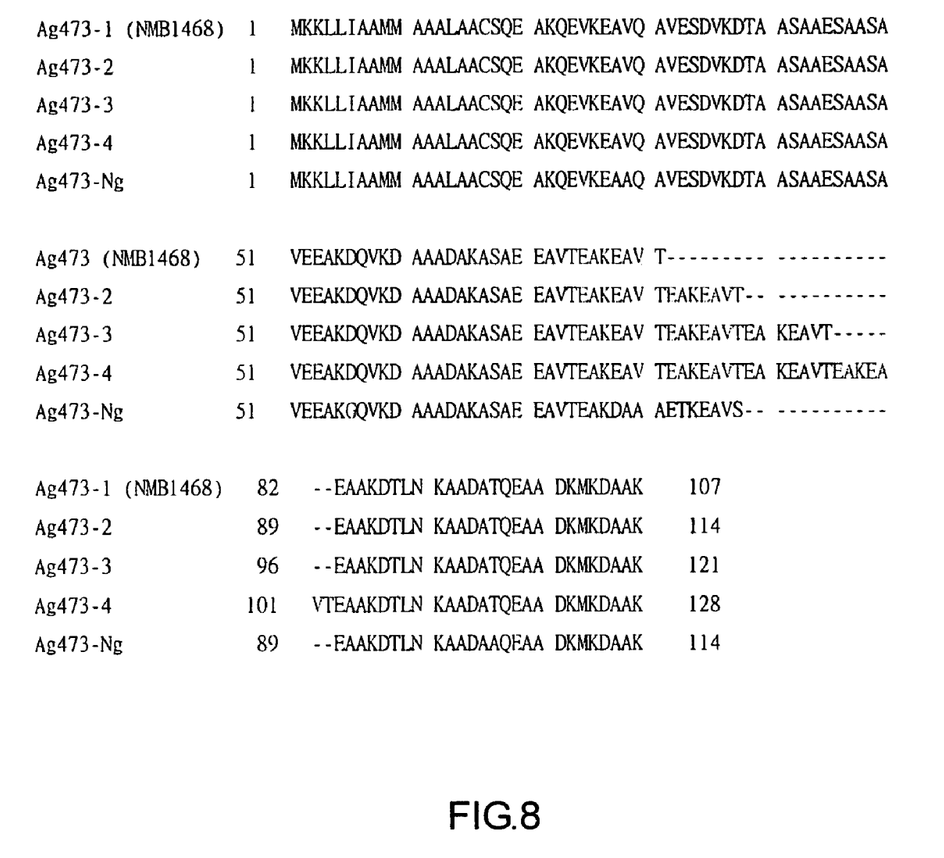
FIG. 8 aligns the amino acid sequences of the five Ag473 variants (SEQ ID No 2, 4, 6, 8and 10); wherein Ag473-1 to Ag473-4 are sequences acquired from *N. meningitidis* and Ag473-Ng from *N. gonorrhoeae.*
Figure 9:
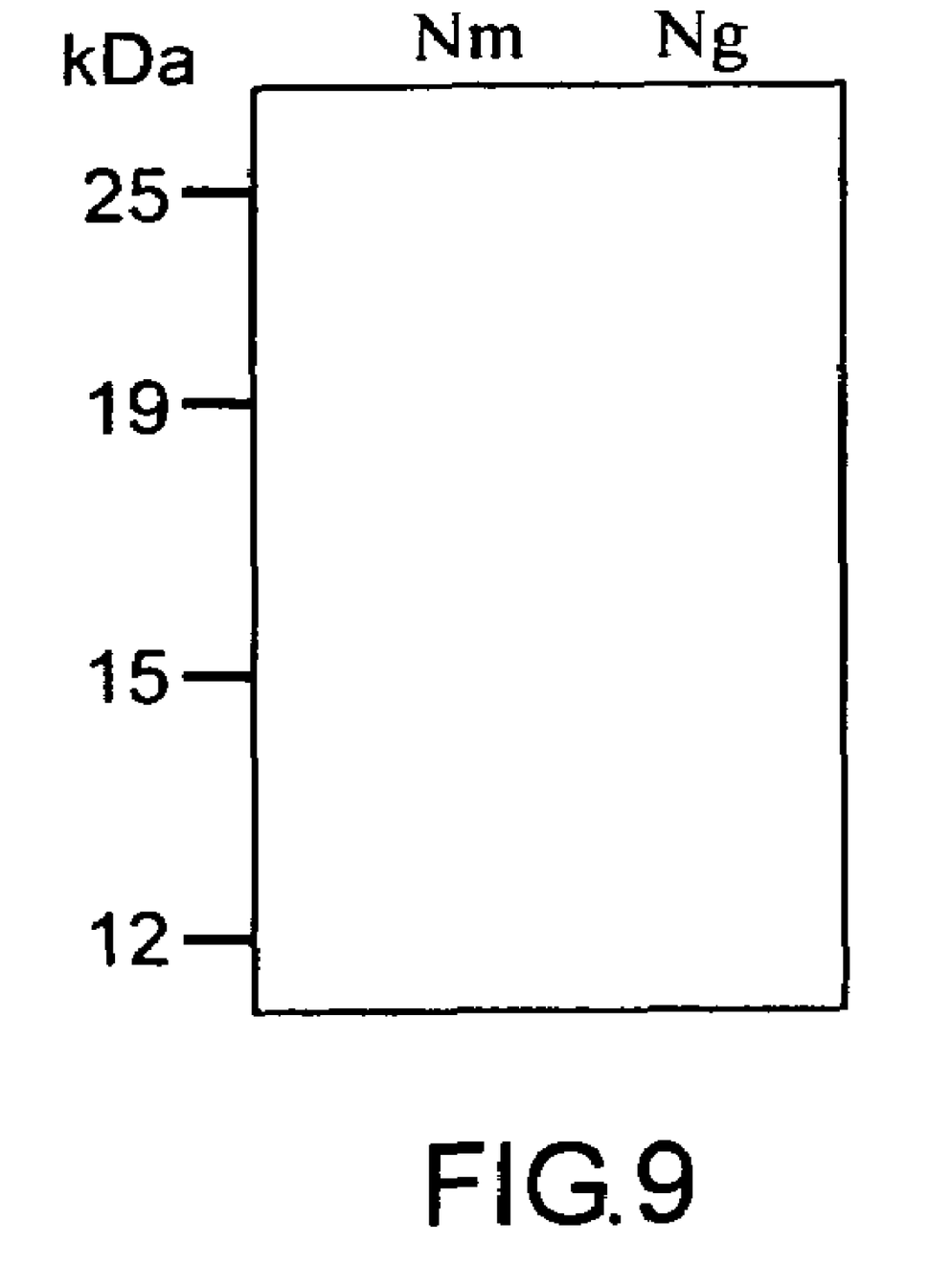
FIG. 9 shows a Western blot of the total proteins from *N. meningitidis* (Nm) and *N. gonorrhoeae* (Ng) detected by monoclonal antibody 4-7-3.

To examine whether the Ag473 is restricted to *N. meningitidis* colony-PCR is performed to detect if the gene is present in other bacteria. Of the strains tested, which include *Campylobacter, Haemophilus, Streptococcus, Pertussis, Klebsiella, Staphylococcus, Micrococcus, Enterococcus, Salmonella, Pseudomonas, Shigella*, and *Neisseria gonorrhoeae*, specific product is observed only in *N. gonorrhoeae*. Sequence analysis shows that the sequence (SEQ ID NO. 9) of *N. gonorrhoeae* PCR product (NG-PCR) reaches 99% identity to that of decoded *N. gonorrhoeae* genome (as shown in FIG. 6). The polynucleotide of NG-PCR reaches 95% of identity to that of SEQ ID NO. 1 (Ag473-2) (as shown in FIG. 7). The deduced amino acid sequence of NG-PCR reaches >90% identity to that of Ag473-2 (as shown in FIG. 8). Accordingly, it is named Ag473-Ng. Western blot analysis of the total proteins from *N. gonorrhoeae* with antibody 4-7-3 confirms that the presence of Ag473 protein (FIG. 9).

The results indicate that Ag473 may have the potential to act as a vaccine composition against both *N. meningitidis* and *N. gonorrhoeae*.

The present invention provides the isolated polypeptide (Ag473), comprising SEQ ID No.2, 4, 6, 8 and 10recognized by antibody 4-7-3which can be used to prepare a vaccine or diagnostic or therapeutic reagent.

Besides, the present invention also provides an isolated polynucleotide, comprising SEQ ID No.1, 3, 5, 7 and 9which can be used to prepare a vaccine or diagnostic or therapeutic reagent. The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An isolated polypeptide comprising the amino acid sequence of SEQ ID NO: 2, 6, or 8.

* * * * *

SEQUENCE LISTING

<160> NUMBER OF SEQ ID NOS: 14

<210> SEQ ID NO 1
<211> LENGTH: 342
<212> TYPE: DNA
<213> ORGANISM: Neisseria meningitidis

<400> SEQUENCE: 1

```
atgaaaaaat tattgattgc cgcaatgatg gcggctgcct tggcagcttg ttcgcaagaa      60
gccaaacagg aggttaagga agcggttcaa gccgttgagt ccgatgttaa agacactgcg     120
gcttctgccg ccgagtctgc cgcttctgcc gtcgaagaag cgaaagacca agtcaaagat     180
gctgcggctg atgcaaaggc aagtgccgag gaagctgtaa ctgaagccaa agaagctgta     240
actgaagcca aagaagctgt aactgaagca gctaaagata ctttgaacaa agctgccgac     300
gcgactcagg aagcggcaga caaaatgaaa gatgccgcca aa                        342
```

<210> SEQ ID NO 2

<211> LENGTH: 114
<212> TYPE: PRT
<213> ORGANISM: Neisseria meningitidis

<400> SEQUENCE: 2

Met Lys Lys Leu Leu Ile Ala Ala Met Met Ala Ala Ala Leu Ala Ala
1               5                   10                  15
Cys Ser Gln Glu Ala Lys Gln Glu Val Lys Glu Ala Val Gln Ala Val
                20                  25                  30
Glu Ser Asp Val Lys Asp Thr Ala Ala Ser Ala Ala Glu Ser Ala Ala
            35                  40                  45
Ser Ala Val Glu Glu Ala Lys Asp Gln Val Lys Asp Ala Ala Ala Asp
        50                  55                  60
Ala Lys Ala Ser Ala Glu Glu Val Thr Glu Ala Lys Glu Ala Val
65                  70                  75                  80
Thr Glu Ala Lys Glu Ala Val Thr Glu Ala Ala Lys Asp Thr Leu Asn
                85                  90                  95
Lys Ala Ala Asp Ala Thr Gln Glu Ala Ala Asp Lys Met Lys Asp Ala
            100                 105                 110
Ala Lys

<210> SEQ ID NO 3
<211> LENGTH: 321
<212> TYPE: DNA
<213> ORGANISM: Neisseria meningitidis

<400> SEQUENCE: 3
atgaaaaaat tattgattgc cgcaatgatg gcggctgcct tggcagcttg ttcgcaagaa      60
gccaaacagg aggttaagga agcggttcaa gccgttgagt ccgatgttaa agacactgcg     120
gcttctgccg ccgagtctgc cgcttctgcc gtcgaagaag cgaaagacca agtcaaagat     180
gctgcggctg atgcaaaggc aagtgccgag gaagctgtaa ctgaagccaa agaagctgta     240
actgaagcag ctaaagatac tttgaacaaa gctgccgacg cgactcagga agcggcagac     300
aaaatgaaag atgccgccaa a                                                321

<210> SEQ ID NO 4
<211> LENGTH: 107
<212> TYPE: PRT
<213> ORGANISM: Neisseria meningitidis

<400> SEQUENCE: 4

Met Lys Lys Leu Leu Ile Ala Ala Met Met Ala Ala Ala Leu Ala Ala
1               5                   10                  15
Cys Ser Gln Glu Ala Lys Gln Glu Val Lys Glu Ala Val Gln Ala Val
                20                  25                  30
Glu Ser Asp Val Lys Asp Thr Ala Ala Ser Ala Ala Glu Ser Ala Ala
            35                  40                  45
Ser Ala Val Glu Glu Ala Lys Asp Gln Val Lys Asp Ala Ala Ala Asp
        50                  55                  60
Ala Lys Ala Ser Ala Glu Glu Val Thr Glu Ala Lys Glu Ala Val
65                  70                  75                  80
Thr Glu Ala Ala Lys Asp Thr Leu Asn Lys Ala Ala Asp Ala Thr Gln
                85                  90                  95
Glu Ala Ala Asp Lys Met Lys Asp Ala Ala Lys
            100                 105

<210> SEQ ID NO 5
<211> LENGTH: 363
<212> TYPE: DNA
<213> ORGANISM: Neisseria meningitidis

<400> SEQUENCE: 5

```
atgaaaaaat tattgattgc cgcaatgatg gcggctgcct tggcagcttg ttcgcaagaa      60
gccaaacagg aggttaagga agcggttcaa gccgttgagt ccgatgttaa agacactgcg     120
gcttctgccg ccgagtctgc cgcttctgcc gtcgaagaag cgaaagacca agtcaaagat     180
gctgcggctg atgcaaaggc aagtgccgag gaagctgtaa ctgaagccaa gaagctgta     240
actgaagcca agaagctgt aactgaagcc aagaagctg taactgaagc agctaaagat     300
actttgaaca agctgccga cgcgactcag gaagcggcag acaaaatgaa agatgccgcc     360
aaa                                                                  363
```

<210> SEQ ID NO 6
<211> LENGTH: 121
<212> TYPE: PRT
<213> ORGANISM: Neisseria meningitidis

<400> SEQUENCE: 6

```
Met Lys Lys Leu Leu Ile Ala Ala Met Met Ala Ala Leu Ala Ala
  1               5                  10                  15

Cys Ser Gln Glu Ala Lys Gln Glu Val Lys Glu Ala Val Gln Ala Val
             20                  25                  30

Glu Ser Asp Val Lys Asp Thr Ala Ala Ser Ala Ala Glu Ser Ala Ala
         35                  40                  45

Ser Ala Val Glu Glu Ala Lys Asp Gln Val Lys Asp Ala Ala Ala Asp
     50                  55                  60

Ala Lys Ala Ser Ala Glu Glu Ala Val Thr Glu Ala Lys Glu Ala Val
 65                  70                  75                  80

Thr Glu Ala Lys Glu Ala Val Thr Glu Ala Lys Glu Ala Val Thr Glu
                 85                  90                  95

Ala Ala Lys Asp Thr Leu Asn Lys Ala Ala Asp Ala Thr Gln Glu Ala
            100                 105                 110

Ala Asp Lys Met Lys Asp Ala Ala Lys
            115                 120
```

<210> SEQ ID NO 7
<211> LENGTH: 384
<212> TYPE: DNA
<213> ORGANISM: Neisseria meningitidis

<400> SEQUENCE: 7

```
atgaaaaaat tattgattgc cgcaatgatg gcggctgcct tggcagcttg ttcgcaagaa      60
gccaaacagg aggttaagga agcggttcaa gccgttgagt ccgatgttaa agacactgcg     120
gcttctgccg ccgagtctgc cgcttctgcc gtcgaagaag cgaaagacca agtcaaagat     180
gctgcggctg atgcaaaggc aagtgccgag gaagctgtaa ctgaagccaa gaagctgta     240
actgaagcca agaagctgt aactgaagcc aagaagctg taactgaagc caaagaagct     300
gtaactgaag cagctaaaga tactttgaac aaagctgccg acgcgactca ggaagcggca     360
gacaaaatga aagatgccgc caaa                                           384
```

<210> SEQ ID NO 8
<211> LENGTH: 128
<212> TYPE: PRT

<213> ORGANISM: Neisseria meningitidis

<400> SEQUENCE: 8

```
Met Lys Lys Leu Leu Ile Ala Ala Met Met Ala Ala Leu Ala Ala
 1               5                  10                  15

Cys Ser Gln Glu Ala Lys Gln Glu Val Lys Glu Ala Val Gln Ala Val
                20                  25                  30

Glu Ser Asp Val Lys Asp Thr Ala Ala Ser Ala Ala Glu Ser Ala Ala
            35                  40                  45

Ser Ala Val Glu Glu Ala Lys Asp Gln Val Lys Asp Ala Ala Ala Asp
    50                  55                  60

Ala Lys Ala Ser Ala Glu Glu Ala Val Thr Glu Ala Lys Glu Ala Val
 65                  70                  75                  80

Thr Glu Ala Lys Glu Ala Val Thr Glu Ala Lys Glu Ala Val Thr Glu
                85                  90                  95

Ala Lys Glu Ala Val Thr Glu Ala Ala Lys Asp Thr Leu Asn Lys Ala
               100                 105                 110

Ala Asp Ala Thr Gln Glu Ala Ala Asp Lys Met Lys Asp Ala Ala Lys
           115                 120                 125
```

<210> SEQ ID NO 9
<211> LENGTH: 342
<212> TYPE: DNA
<213> ORGANISM: Neisseria gonorrhoeae

<400> SEQUENCE: 9

```
atgaaaaaat tattgattgc cgcaatgatg gcggctgcct tggcagcttg ttcgcaagaa    60
gccaaacagg aggttaaaga agcggcccaa gccgttgagt ccgatgttaa agacactgcg   120
gcttctgccg ccgagtctgc cgcttctgcc gtcgaagaag cgaaaggcca agtcaaagat   180
gctgcggctg atgcaaaggc aagtgccgag gaagctgtaa ctgaagccaa agacgcggca   240
gccgaagcca agaagcggt aagcgaagcg gctaaagaca ctttgaacaa agccgccgac   300
gcgactcagg aagcggcaga caaaatgaaa gatgccgcca aa                     342
```

<210> SEQ ID NO 10
<211> LENGTH: 114
<212> TYPE: PRT
<213> ORGANISM: Neisseria gonorrhoeae

<400> SEQUENCE: 10

```
Met Lys Lys Leu Leu Ile Ala Ala Met Met Ala Ala Leu Ala Ala
 1               5                  10                  15

Cys Ser Gln Glu Ala Lys Gln Glu Val Lys Glu Ala Ala Gln Ala Val
                20                  25                  30

Glu Ser Asp Val Lys Asp Thr Ala Ala Ser Ala Ala Glu Ser Ala Ala
            35                  40                  45

Ser Ala Val Glu Glu Ala Lys Gly Gln Val Lys Asp Ala Ala Ala Asp
    50                  55                  60

Ala Lys Ala Ser Ala Glu Glu Ala Val Thr Glu Ala Lys Asp Ala Ala
 65                  70                  75                  80

Ala Glu Thr Lys Glu Ala Val Ser Glu Ala Ala Lys Asp Thr Leu Asn
                85                  90                  95

Lys Ala Ala Asp Ala Ala Gln Glu Ala Ala Asp Lys Met Lys Asp Ala
               100                 105                 110

Ala Lys
```

```
<210> SEQ ID NO 11
<211> LENGTH: 342
<212> TYPE: DNA
<213> ORGANISM: Neisseria gonorrhoeae

<400> SEQUENCE: 11
ttggcggcat ctttcatttt gtctgccgct tcctgagccg cgtcggcggc tttgttcaaa    60
gtgtctttag ccgcttcgct taccgcttct ttggcttcgg ctgccgcgtc tttggcttca   120
gttacagctt cctcggcact tgcctttgca tcagccgcag catctttgac ttggcctttc   180
gcttcttcga cggcagaagc ggcagactcg gcggcagaag ccgcagtgtc tttaacatcg   240
gactcaacgg cttgggccgc ttctttaacc tcctgtttgg cttcttgcga acaagctgcc   300
aaggcagccg ccatcattgc ggcaatcaat aatttttttca tg                     342

<210> SEQ ID NO 12
<211> LENGTH: 342
<212> TYPE: DNA
<213> ORGANISM: Neisseria gonorrhoeae

<400> SEQUENCE: 12
ttggcggcgt ctttcatttt gtctgccgct tcctgagccg cgtcggcagc tttgttcaaa    60
gtgtctttag ccgcttcgct taccgcttct ttggcttcgg ctgccgcgtc tttggcttca   120
gttacagctt cctcggcact tgcctttgca tcagccgcag catctttgac ttggcctttc   180
gcttcttcga cggcagaagc ggcagactcg gcggcagaag ccgcagtgtc tttaacatcg   240
gactcaacgg cttgggccgc ttctttaacc tcctgtttgg cttcttgcga acaagctgcc   300
aaggcagccg ccatcattgc ggcaatcaat aatttttttca tg                     342

<210> SEQ ID NO 13
<211> LENGTH: 21
<212> TYPE: DNA
<213> ORGANISM: Neisseria sp.

<400> SEQUENCE: 13
gaagctgtaa ctgaagccaa a                                              21

<210> SEQ ID NO 14
<211> LENGTH: 7
<212> TYPE: PRT
<213> ORGANISM: Neisseria sp.

<400> SEQUENCE: 14

Glu Ala Val Thr Glu Ala Lys
 1               5
```